United States Patent

Hedrich

[11] 4,335,044
[45] Jun. 15, 1982

[54] PLANT GROWTH REGULATING PERFLUOROACYL ARYLTHIOUREIDO ISOINDOLEDIONES

[75] Inventor: Loren W. Hedrich, Orange, Tex.

[73] Assignee: Gulf Oil Corporation, Pittsburgh, Pa.

[21] Appl. No.: 262,279

[22] Filed: May 11, 1981

Related U.S. Application Data

[62] Division of Ser. No. 175,000, Aug. 4, 1980, Pat. No. 4,289,527.

[51] Int. Cl.³ .......................................... C07D 209/48
[52] U.S. Cl. ................................................... 548/475
[58] Field of Search ........................ 260/326 S, 326 N

[56] References Cited

U.S. PATENT DOCUMENTS 4,264,502  4/1981  Patel et al. ........................ 260/326 S Primary Examiner—Catherine L. Mills
Attorney, Agent, or Firm—Deane E. Keith; Forrest D. Stine; Carl A. Cline

[57] ABSTRACT

A novel class of compounds which are useful as plant growth regulators is disclosed, having the general structural formula:

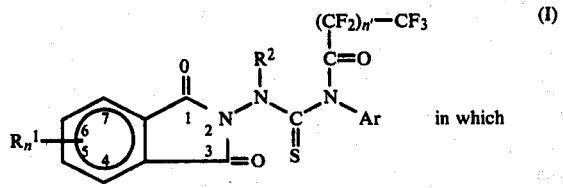

in which $R^1$ is; $C_1$ to $C_4$ alkyl, nitro or halo and n is zero or an integer from 1 to 4

$R^2$ is; $C_1$ to $C_4$ alkyl, or benzyl, n' is zero, 1 or 2 and

Ar is; naphthyl, phenyl or phenyl bearing thereon from one to three of the substituents: cyano, benzyloxy, nitro, bromo, chloro, trifluoromethyl and $C_1$ to $C_4$ alkyl, alkenyl, alkoxy alkylthio and alkyl-substituted amino.

24 Claims, No Drawings

PLANT GROWTH REGULATING PERFLUOROACYL ARYLTHIOUREIDO ISOINDOLEDIONES

This is a division of application Ser. No. 175,000 filed Aug. 4, 1980, now U.S. Pat. No. 4,289,527.

DESCRIPTION OF THE INVENTION

Plant growth regulators are chemical compounds which have the ability to affect the physiological process of plants, resulting in several types of observable effects, which may be classified as follows:

The auxin effect is a stimulation of cell elongation or enlargement. The cytokinin effect is observed as stimulation of cell division. The gibberellin effect is a stimulation of cell division or enlargement, or both. The effect of ethylene gas on growth is a stimulation of swelling or isodiametric growth of stems and roots. Besides these effects there are various growth regulators which inhibit a portion of, or a combination of physiological processes. Among the growth regulators are compounds which are produced naturally by the plants and are called plant hormones. Most of the natural plant hormones exhibit combinations of growth regulatory effects, which overlap with other hormones. In general, the synthesis and use of the natural plant hormones to modify and improve the utility of crop plants is not successful because the resulting effects are too complex and are beset with undesirable side effects. As a consequence, with few exceptions, the commercially useful growth regulators are compounds which are chemically unrelated to the naturally occurring hormones and exhibit the recognizable growth regulator effects in different and more useful combinations. There are now more than a score of such commercial growth regulators in extensive use in agriculture. Among the known and desired commercial uses for plant growth regulators are the following:

Increase or induce flowering (pineapple).
Increase blossom set, pod set, seed set, and/or fruit set (prevent abortion of flowers or withered blossoms).
Increase size of fruits, vegetables, seed, and/or tubers (grapes, soybeans, sugar beets, etc).
Decrease size of fruit, vegetables, seed, and/or tubers (potatoes, and grapefruits).
Increase number of tillers (cereals).
Increase number of shoots from crown (alfalfa).
Increase branching (soybeans) or widen branches (apples).
Reduce height (shortened internodes) in crops and ornamentals (cereals and mums).
Growth retardant (turf, cotton, perennial legumes in no-till corn).
Enhance yields of corn by larger ears, better filled ears and/or more ears per plant.
Increase nutritive value of seeds, fruits, vegetables, forages, etc. (protein content).
Reduce transpiration (drought resistance).
Reduce respiration (potatoes or sugar beets in storage).

However, many much-desired growth regulatory effects have not yet been achieved. Although growth regulation has been an active field of research for over fifty years, the fundamental mechanisms of the various types of growth regulatory action have not been elucidated. (See *Chemical and Engineering News*, Oct. 9, 1978, pages 18–26 and 31–34).

This invention is directed to a new class of growth regulators which exhibit a variety of useful effects, including increasing fruit set on plants of species as different as *Lycopersicum esculentum* and *Soja max*. This invention is also directed to methods of synthesis of the novel compounds and use of the compounds to regulate growth of plants.

Briefly, the novel class of growth regulator compounds has the general structural formula:

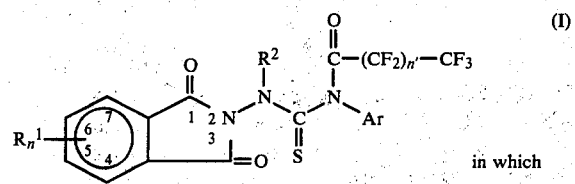

in which $R^1$ is; $C_1$ to $C_4$ alkyl, nitro or halo and $n$ is zero or an integer from 1 to 4
$R^2$ is $C_1$ to $C_4$ alkyl, or benzyl, $n'$ is zero, 1 or 2 and
Ar is; naphthyl, phenyl or phenyl bearing thereon from one to three of the substituents: cyano, benzyloxy, nitro, bromo, chloro, trifluoromethyl and $C_1$ to $C_4$ alkyl, alkenyl, alkoxy, alkylthio and alkyl-substituted amino.

The aforementioned compounds are employed to regulate the growth of plants by applying an effective amount to the plants, the seed or the soil, preferably in combination with an inert carrier or diluent and a surface active agent, according to customary practice in the art.

SYNTHESIS OF THE GROWTH REGULATORS

The novel compounds of this invention may be produced from commercially available raw materials by means of procedures based on those outlined and specifically illustrated below:

N-Methyl-N-(phenylthiocarbamoyl)-2-amino-1H-isoindole-1,3-(2H)-dione (II) has been prepared by the cyclization of 2-(2-carboxybenzoyl)-1-methyl-N-phenyl-hydrazinethiocarboxamide with N,N'-dicyclohexylcarbodiimide, as outlined below:

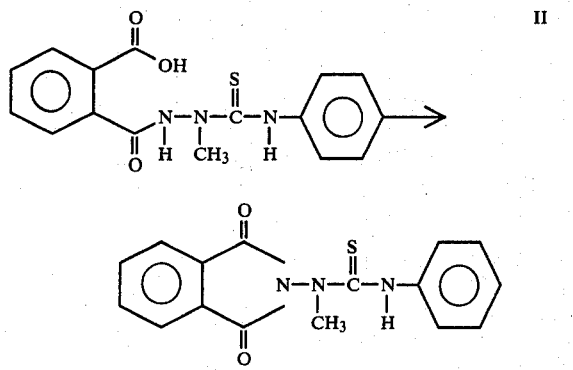

Similarly, commercially available ring substituted phthalic anhydrides and substituted 2-carbomethoxybenzoyl chlorides, made by conventional methods may be condensed with N-methyl and 1-methylhydrazine-thiocarboxamides to give the corresponding specific compounds of formula (IV), as in the following outline of synthesis procedures.

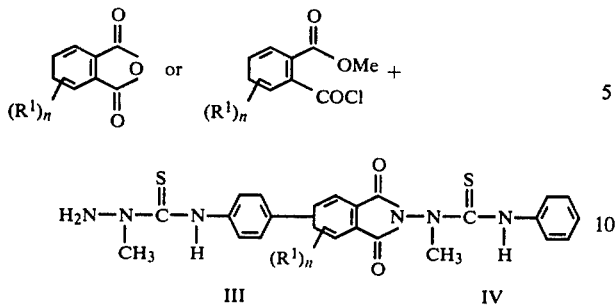

Below are specific illustrative procedures. The identity of the product was confirmed in each example by means of infrared and nuclear magnetic resonance spectra. All melting points are uncorrected.

2-methylamino-N-phenylthiocarbamoyl-1H-isoindole-1,3-(2H)dione (II).

To an ice-cold solution of 8.25 g (0.025 mole) of 2-(2-carboxybenzoyl)-1-methyl-N-phenylhydrazinethiocarboxamide in 225 ml of 1,2-dimethoxyethane at 0° C., a solution of 5.5 g (0.027 mole) of N,N'-dicyclohexylcarbodiimide was added dropwise below 5° C. with stirring. The mixture was stirred in the ice bath and then left at room temperature overnight. The mixture was filtered to remove N,N'-dicyclohexylurea and the filtrate was evaporated below 40° C., under vacuum, to give a yellow amorphous solid which was stirred in 100 ml of dry ether and warmed gently. The ether solution was allowed to stand for a few hours and filtered to give 4.6 g (59%) of whitish yellow crystals, m.p. 142°–144°.

Recrystallization from ethyl acetate-hexane gave whitish crystals, m.p. 151°–153°.

Mass spectrum: M+311

2-methylamino-4-methyl-N-phenylthiocarbamoyl-1H-isoindole-1,3-(2H)dione (IV, R'=4-CH$_3$).

To a solution of 6.8 g (0.037 mole) of 1-methyl-N-phenylhydrazinethiocarboxamide (III) and 3.0 g of pyridine in 100 ml dry dimethoxyethane, 2-carbomethoxy-6-methylbenzoyl chloride (8.0 g, 0.037 mole) was added and the resulting mixture was stirred at room temperature for 60 hours. The solvent was distilled and the residue was taken up in ethyl acetate, filtered and dried over anhydrous magnesium sulfate. Removal of the solvent gave 10 g (83%) of the desired product, m.p. 110°–115° (dec.).

N-perfluoropropionylphenylthiocarbamoyl-2-methylamino-1H-isoindole-1,3-(2H)dione (I, Ar=phenyl, n=1).

A solution of 2-methylamino-N-phenylthiocarbamoyl-1H-isoindole-1,3-(2H)dione (II) (3.1 g, 0.01 mole) in 50 ml of dioxane and 3.0 g (0.03 mole) of triethylamine was cooled to 5° in an ice-bath. Perfluoropropionic anhydride (3.3 g, 0.015 mole) was added dropwise. Following the addition the ice-bath was removed and the clear yellow solution was stirred 16 hr. at room temperature. The solution was poured into 500 ml of ice-water and stirred for 15 minutes. The pale yellow solid was removed by filtration affording 2.5 g (55%) of the desired product, m.p. 149°–154°.

Specific compounds which have been prepared by means of procedures of the type illustrated above are listed below in Table 1.

TABLE 1

Compounds of the formula

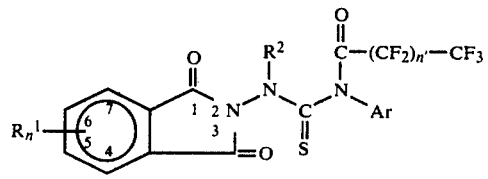

| Compound No. | $R_n{}^1$ | $R^2$ | n' | Ar | M.P. °C. | Comments on Utility |
|---|---|---|---|---|---|---|
| 4328 | n=0 | CH$_3$ | 0 | phenyl | 156–159 | Promotes tillering in oats |
| 4494 | n=0 | CH$_3$ | 2 | phenyl | oil | Promotes tillering in oats |
| 4495 | n=0 | CH$_3$ | 1 | phenyl | 149–154 | Promotes tillering in oats |
| 4591 | n=0 | CH$_3$ | 0 | 2,4(CH$_3$)$_2$phenyl | 173–175 | |
| 4592 | n=0 | CH$_3$ | 1 | 2,4(CH$_3$)$_2$phenyl | 163–165 | |
| 4593 | n=0 | CH$_3$ | 0 | 4-Cl phenyl | 145–150 | Promotes tillering in oats |
| 4594 | n=0 | CH$_3$ | 0 | 4-F phenyl | oil | Promotes tillering in oats |
| 4829 | n=0 | —CH$_3$ | 0 | 3-bromophenyl | 128–130 | |
| 4841 | n=0 | —CH$_3$ | 0 | 2-naphthyl | 90°(dec.) | |
| 4842 | " | " | 0 | 4-cyanophenyl | 155–160 | |
| 4843 | " | " | 0 | 4-phenoxybenzyl | 94(dec.) | |
| 4844 | " | " | 0 | 4-isopropylphenyl | 95(dec.) | |
| 4845 | " | " | 0 | 4-ethoxyphenyl | 137(dec.) | |
| 4853 | " | —H | 0 | 4-isopropylphenyl | 62(dec.) | |
| 4913 | " | —CH$_3$ | 0 | 2,3-dimethylphenyl | 178–182 | |
| 4916 | " | " | 0 | 4-bromophenyl | 165–175 | |
| 4917 | " | " | 0 | 3,5-dimethylphenyl | 70(dec.) | |
| 4919 | " | " | 0 | 4-carbethoxyphenyl | 60(dec.) | |
| 4921 | " | —CH$_2$CH$_3$ | 0 | phenyl | — | |
| 4922 | " | —CH$_3$ | 0 | 3-fluorophenyl | — | |
| 4924 | 5-CH$_3$ | " | 0 | phenyl | 69–72 | |
| 4927 | n=0 | " | 0 | 4-fluoro-2-methyl-phenyl | 95–100(dec.) | |
| 4950 |ن=0 | allyl | 0 | phenyl | oil | |
| 4951 | " | —CH$_3$ | 0 | 3-methylthiophenyl | 151–154 | |
| 4953 | " | " | 0 | 4-phenoxyphenyl | 62–70(dec.) | |

TABLE 1-continued

Compounds of the formula $$R_n^1 - \underset{7\ 6\ 5\ 4}{\bigcirc} - \overset{O}{\underset{\parallel}{C}} - \underset{1}{N} - \overset{R^2}{\underset{2}{N}} - \overset{O}{\underset{\parallel}{C}} - (CF_2)_{n'} - CF_3$$
(with 3=O, C=S, Ar on N)

| Compound No. | $R_n^1$ | $R^2$ | n' | Ar | M.P. °C. | Comments on Utility |
|---|---|---|---|---|---|---|
| 4955 | " | " | 0 | 1-naphthyl | 74(dec.) | |

USE OF THE GROWTH REGULATORS

In highly active compounds, both growth regulating and phytotoxic effects are pre-emergent and post-emergent application are often readily apparent. These effects may be demonstrated by means of the following illustrative procedures.

PRE-EMERGENT APPLICATION

Disposable paper trays about 2½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule:

DEGREE OF EFFECT

0 = no effect
1 = slight effect, plants recovered
2 = moderate effect, injury to 26 to 75 percent
3 = severe effect, injury to 76 to 99 percent of foliage
4 = maximum effect (all plants died)

POST-EMERGENT APPLICATION

Several species of plants were grown in potting soil in disposable styrofoam type trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulator. Plant injury was again rated according to the schedule disclosed above and observations of growth regulator effects were observed and recorded as follows:

| Effect | Abbreviation in Tables |
|---|---|
| Formative effect on new growth | F |
| Epinasty | E |
| Growth reduction | G |
| Non-emergence | K |
| Necrosis | N |

In Table 2 below there are tabulated observations of pre- and post-emergent herbicidal and growth regulator effects of the compounds.

TABLE 2

EFFECTS ON PLANT SPECIES

| | Preemergent Effects | | | | | | Postemergent Effects | | | | | |
|---|---|---|---|---|---|---|---|---|---|---|---|---|
| Compound No. | Crabgrass | Coxcomb | Brome | Millet | Radish | Sugar Beet | Millet | Alfalfa | Oat | Radish | Sugar Beet | Tomato |
| 4328 | F3G3 | F3G2 | F3 G3 | F3 G3 | F3 G2 | F3 G2 | N2 F2 | F3 G2 | F1 | F2 G1 | F2 | F3 G1 |
| 4494 | K4 | F3 G3 | F3 G3 | F3 G3 | F3 G2 | F3 G3 | F1 N1 G1 | F3 G2 | F2 | F1 G1 | F2 G1 | F3 |
| 4495 | F3 G3 | K4 | F3 G3 | F3 G3 | F2 G2 | F2 G2 | N4 G3 | F3 G1 | F2 G1 | F2 G1 | F2 | F3 |
| 4591 | F1 G1 | G2 | K3 F3 | F3 G3 | F1 | F1 | F1 | F1 | 0 | 0 | F1 | F2 |
| 4592 | F1 G1 | F1 | F3 G1 | F3 G2 | 0 | F1 | 0 | F1 | 0 | F1 | F1 | 0 |
| 4593 | F3 G3 | F3 G3 | K4 | F3 G3 | F3 G3 | F3 G3 | F2 G2 | F3 G3 | F3 G2 | F3 G2 | F3 G3 | F3 G1 |
| 4594 | F3 G3 | F3 G3 | F3 G3 | F3 G3 | F3 G3 | F3 G3 | F2 G1 | F3 G3 | F2 G1 | F2 G1 | F3 G2 | F3 |

POST-EMERGENT APPLICATION AT LOWER RATES ON 24 SPECIES

Twenty-four species of plants were grown in potting soil in disposable styrofoam trays and tomatoes were grown in four-inch pots in the greenhouse. Aqueous spray formulations were prepared and the growing plants were sprayed at a spray volume of 40 gallons per acre and application rates of 3 lb. and 1 lb. per acre. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of warm water. Of this spray mixture, a 50 ml portion was used to spray the plants at a rate of 3 lb. per acre of sprayed area. The remaining 30 ml was diluted to 90 ml with warm water and was used to spray the plants at a rate of 1 lb. per acre. One large, more mature tomato plant was included in the test along with the other, smaller growing plants. For comparative purposes, plants were also sprayed at a spray volume of 40 gallons per acre with a spray mixture containing no growth regulator.

Approximately fifteen days after spraying, the plants were observed and the results were evaluated according to the schedule disclosed above. Results obtained with representative compounds are presented in Table 3. The test species are as follows:

| Number | Common Name | Scientific Name |
|---|---|---|
| I | Pigweed | *Amaranthus retroflexus* |
| II | Lambsquarters | *Chenopodium album* |
| III | Crabgrass | *Digitaria sanguinalis* |
| IV | Downey brome | *Bromus tectorum* |
| V | Giant foxtail | *Setaria feberii* |
| VI | Nutsedge | *Cyperus esculentus* |
| VII | Peanuts | *Arachis hypogaea* |
| VIII | Cotton | *Gossypium herbaceum* |
| IX | Tomato | *Lycopersicum esculentum* |
| X | Sugar beets | *Beta vulgaris* |
| XI | Wild buckwheat | *Polygonum convolvulus* |
| XII | Wild mustard | *Brassica kaber* |
| XIII | Mature tomato plant | *Lycopersicum esculentum* |
| XIV | Cocklebur | *Xanthium pensylvanicum* |
| XV | Morning glory | *Ipomea purpurea* |
| XVI | Soybeans | *Soja max* |
| XVII | Barnyard grass | *Echinochloa crusgalli* |
| XVIII | Green foxtail | *Setaria viridis* |
| XIX | Alfalfa | *Medicago sativa* |
| XX | Corn | *Zea mays* |
| XXI | Grain sorghum | *Sorghum vulgare* |
| XXII | Shattercane | *Sorghum bicolor* |
| XXIII | Wheat | *Triticum aestivum* |
| XXIV | Wild oats | *Avena fatua* |
| XXV | Rice | *Oryza sativa* |

Observations of increase of fruit set and tillering, cotton defoilation, etc. are noted under "Comments".

TABLE 3

POST-EMERGENT EFFECTS ON 24 SPECIES

| Species | Appl'n. Rate (lb/A) | 4829 | 4841 | 4842 | 4843 | 4844* | 4845 | 4853 | 4913 | 4916 | 4917 | 4919 |
|---|---|---|---|---|---|---|---|---|---|---|---|---|
| I | 3 | 0 | F1G1 | F1 | F3G3 | F1 | F3G3 | F3G2 | F3G3 | F3G3 | F3G3 | F3G2 |
|   | 1 | 0 | 0 | 0 | F1 | 0 | F2G2 | F1 | F2G2 | F2G1 | F3G3 | F3G2 |
| II | 3 | 0 | F1G1 | 0 | F3G3 | 0 | F3G3 | F3G3 | F3G3 | F3G3 | F3G3 | F3G3 |
|   | 1 | 0 | F1 | 0 | F2G1 | 0 | F2G1 | F1 | F2G2 | F2G2 | F3G3 | F3G2 |
| III | 3 | 0 | 0 | 0 | 0 | 0 | 0 | 0 | F1G1 | 0 | F2G2 | G1 |
|   | 1 | 0 | 0 | 0 | 0 | 0 | 0 | 0 | F1G1 | 0 | F1G1 | 0 |
| IV | 3 | 0 | 0 | 0 | 0 | 0 | 0 | 0 | 0 | 0 | F1G1 | 0 |
|   | 1 | 0 | 0 | 0 | 0 | 0 | 0 | 0 | 0 | 0 | 0 | 0 |
| V | 3 | 0 | 0 | 0 | 0 | 0 | 0 | F1 | F2G1 | F1 | F3G2 | F1 |
|   | 1 | 0 | 0 | 0 | 0 | 0 | 0 | 0 | F1 | 0 | F2G1 | 0 |
| VI | 3 | 0 | 0 | 0 | 0 | 0 | 0 | 0 | 0 | 0 | G1 | 0 |
|   | 1 | 0 | 0 | 0 | 0 | 0 | 0 | 0 | 0 | 0 | 0 | 0 |
| VII | 3 | 0 | 0 | 0 | 0 | 0 | F1 | 0 | F1 | F1 | F1 | 0 |
|   | 1 | 0 | 0 | 0 | 0 | 0 | 0 | 0 | 0 | 0 | 0 | 0 |
| VIII | 3 | N1 | N2 | F1G1 | F3N2 | 0 | F3G2 | F1N1 | F3G2 | F3G2 | F3G2 | F3N1 |
|   | 1 | 0 | 0 | F1 | F3N2 | 0 | F2 | N1 | F3 | F3G1 | F2 | F1 |
| IX | 3 | 0 | F1N1 | F2 | F1 | N1 | F3G3 | F1 | F3G1 | F3G3 | F3G2 | F2 |
|   | 1 | 0 | 0 | 0 | 0 | 0 | F3G1 | 0 | F2 | F3G2 | F2 | F1 |
| X | 3 | F1 | F1 | F1 | F3G1 | F1 | F2G1 | F2 | F3G2 | F3G2 | F3G2 | F3G3 |
|   | 1 | 0 | 0 | F1 | F1 | F1 | F2 | F1 | G1F2 | F2G1 | F2G1 | G1F2 |
| XI | 3 | 0 | 0 | 0 | F3G2 | F1 | F2G1 | F2G2 | F3G3 | F3G3 | F3G2 | F2G2 |
|   | 1 | 0 | 0 | 0 | F2 | 0 | F1 | F2 | F2G2 | F2G2 | F3G2 | F1G1 |
| XII | 3 | 0 | 0 | F1 | F3G2 | 0 | F3G3 | F3G3 | F3G2 | F3G2 | F1G1 | F1 |
|   | 1 | 0 | 0 | 0 | F1 | 0 | F2 | F1 | F2G1 | F2G1 | F1 | 0 |
| XIII | 3 | N1 | F2 | F2 | F3 | 0 | F3 | F2 | F3 | F3G3 | F3G3 | F2 |
|   | 1 | 0 | 0 | 0 | F2 | 0 | F2 | F1 | F2 | F3 | F3G1 | 0 |
| XIV | 3 | 0 | 0 | 0 | F1 | 0 | F1 | F1 | F2 | F2G1 | F2G1 | 0 |
|   | 1 | 0 | 0 | 0 | 0 | 0 | 0 | 0 | F1 | F1 | F2 | 0 |
| XV | 3 | 0 | F1 | 0 | F2G1 | 0 | F2G1 | F2G1 | F3G2 | F3G2 | F3G2 | F1 |
|   | 1 | 0 | 0 | 0 | F1 | 0 | 0 | F1 | F1G1 | F2G1 | F2G2 | 0 |
| XVI | 3 | N2F1 | F1N1 | F1 | F3G3 | F2N1 | F3G3 | F3G3 | F3G3 | F3G3 | F3G3 | F2 |
|   | 1 | 0 | 0 | 0 | F3G1 | 0 | F2G1 | F2G1 | F2G2 | F3G3 | F3G3 | N1 |
| XVII | 3 | 0 | 0 | 0 | 0 | 0 | G2F1 | F2 | F2G1 | F1G1 | F2G1 | 0 |
|   | 1 | 0 | 0 | 0 | 0 | 0 | 0 | 0 | F1 | 0 | F1G1 | 0 |
| XVIII | 3 | 0 | 0 | 0 | 0 | 0 | F3G2 | F1 | F2G2 | F1G1 | F3G2 | F1 |
|   | 1 | 0 | 0 | 0 | 0 | 0 | F1 | 0 | F1 | 0 | F2G1 | 0 |
| XIX | 3 | F2G1 | F1 | F1 | F3G2 | F2 | F3G2 | F3 | F3G3 | F3G3 | F3G3 | F2 |
|   | 1 | 0 | F1 | 0 | F3G1 | F1 | F2 | F2 | F3 | F2 | F3G3 | F1 |
| XX | 3 | 0 | F1G1 | 0 | 0 | 0 | 0 | 0 | F3G2 | 0 | F2 | 0 |
|   | 1 | 0 | 0 | 0 | 0 | 0 | 0 | 0 | F1 | 0 | F1 | 0 |
| XXI | 3 | 0 | 0 | 0 | 0 | 0 | 0 | F1 | F3G2 | F2 | F3G1 | 0 |
|   | 1 | 0 | 0 | 0 | 0 | 0 | 0 | 0 | F1 | F1 | F2 | 0 |
| XXII | 3 | 0 | 0 | 0 | 0 | 0 | 0 | 0 | F3G2 | F1G1 | F3G2 | 0 |
|   | 1 | 0 | 0 | 0 | 0 | 0 | 0 | 0 | F1 | 0 | F2 | 0 |
| XXIII | 3 | 0 | 0 | 0 | 0 | 0 | F1G1 | G1 | F2G2 | F1 | F2G2 | 0 |

TABLE 3-continued
POST-EMERGENT EFFECTS ON 24 SPECIES

|  |  |  |  |  |  |  |  |  |  |  |  |  |
|---|---|---|---|---|---|---|---|---|---|---|---|---|
|  | 1 | 0 | 0 | 0 | 0 | 0 | 0 | 0 | F1 | 0 | F2G1 | 0 |
| XXIV | 3 | 0 | 0 | 0 | 0 | 0 | 0 | 0 | F2G1 | F1 | F2G1 | 0 |
|  | 1 | 0 | 0 | 0 | 0 | 0 | 0 | 0 | 0 | 0 | F1G1 | 0 |
| XXV | 3 | 0 | 0 | 0 | 0 | 0 | 0 | 0 | F2G1 | F1 | F2G1 | 0 |
|  | 1 | 0 | 0 | 0 | 0 | 0 | 0 | 0 | 0 | 0 | F2 | 0 |
| Comments |  |  |  |  | Cotton defoliant | *Rates are 1½ and ¼ lb/A. | Tillering, fruit set |  | Tillering Fruit set | Fruit set | Tillering Fruit set | Fruit set |

| Species | Appl'n. Rate (lb/A) | Compound Nos. |  |  |  |  |  |  |  |
|---|---|---|---|---|---|---|---|---|---|
|  |  | 4921 | 4922 | 4924 | 4927 | 4950* | 4951 | 4953* | 4955 |
| I | 3 | F2G2 | F2G2 | F1 | F3G3 | F2G1 | F1 | F3G2 | F3G2 |
|  | 1 | F2G1 | F2G1 | F1 | F3G3 | 0 | 0 | F1 | F3G2 |
| II | 3 | F2G2 | F2G2 | F1G1 | F3G3 | F2G2 | F1 | F3G2 | F3G3 |
|  | 1 | F2G2 | F2G2 | F1 | F3G3 | F1 | 0 | F2G1 | F3G2 |
| III | 3 | 0 | 0 | 0 | F2G2 | 0 | 0 | 0 | F1 |
|  | 1 | 0 | 0 | 0 | F1 | 0 | 0 | 0 | 0 |
| IV | 3 | 0 | 0 | 0 | F1G1 | 0 | 0 | 0 | 0 |
|  | 1 | 0 | 0 | 0 | 0 | 0 | 0 | 0 | 0 |
| V | 3 | 0 | 0 | 0 | F3G2 | 0 | 0 | 0 | 0 |
|  | 1 | 0 | 0 | 0 | F1 | 0 | 0 | 0 | 0 |
| VI | 3 | 0 | 0 | 0 | 0 | 0 | 0 | 0 | 0 |
|  | 1 | 0 | 0 | 0 | 0 | 0 | 0 | 0 | 0 |
| VII | 3 | 0 | 0 | 0 | F1 | 0 | 0 | 0 | 0 |
|  | 1 | 0 | 0 | 0 | 0 | 0 | 0 | 0 | 0 |
| VIII | 3 | F1 | F2 | F1 | F3G2 | F1 | F2 | F1 | F3G2 |
|  | 1 | F1 | F2 | 0 | F2 | 0 | F1 | 0 | F2 |
| IX | 3 | F2 | F2 | F1 | F2 | F2 | F3 | F1 | F3G3 |
|  | 1 | F1 | F1 | 0 | F2 | F1 | F2 | 0 | F2 |
| X | 3 | F2 | F2G1 | F1 | F3G2 | F2G1 | F2 | F2G1 | F3G3 |
|  | 1 | F1 | F2 | F1 | F2G1 | F1 | F1 | F1 | F2G1 |
| XI | 3 | F1 | F1 | 0 | F3G3 | F2G2 | F2G2 | F2G2 | F3G3 |
|  | 1 | 0 | 0 | 0 | F3G2 | 0 | F1 | F1 | F2G2 |
| XII | 3 | F1 | F2 | F2 | F1G1 | 0 | F2 | F1 | F2G1 |
|  | 1 | 0 | F1 | 0 | F1G1 | 0 | 0 | 0 | F1 |
| XIII | 3 | F3 | F3 | F3 | F3G2 | F2 | F2 | F1 | F3 |
|  | 1 | F2 | F2 | F2 | F3 | 0 | F1 | 0 | F3 |
| XIV | 3 | F1 | F1 | 0 | F1 | 0 | 0 | 0 | F1 |
|  | 1 | 0 | F1 | 0 | F1 | 0 | 0 | 0 | 0 |
| XV | 3 | F1 | F1 | F1 | F3G3 | 0 | F1 | 0 | F2G2 |
|  | 1 | 0 | F1 | 0 | F2G2 | 0 | 0 | 0 | F1 |
| XVI | 3 | F3G2 | F3G2 | N1F2 | F3G3 | N1F1 | F3G2 | F2 | F3G3 |
|  | 1 | F1N1 | F3G2 | N1 | F3G3 | 0 | F2G1 | F1 | F2 |
| XVII | 3 | 0 | 0 | 0 | F2G2 | 0 | 0 | 0 | 0 |
|  | 1 | 0 | 0 | 0 | F2G1 | 0 | 0 | 0 | 0 |
| XVIII | 3 | 0 | 0 | 0 | F3G2 | 0 | 0 | 0 | F1 |
|  | 1 | 0 | 0 | 0 | F2G1 | 0 | 0 | 0 | 0 |
| XIX | 3 | F2 | F2 | F2 | F3G3 | F1 | F2 | F1 | F3G2 |
|  | 1 | F1 | F1 | F2 | F2G1 | F1 | F1 | F1 | F2 |
| XX | 3 | 0 | 0 | 0 | F2G1 | 0 | 0 | 0 | 0 |
|  | 1 | 0 | 0 | 0 | F1 | 0 | 0 | 0 | 0 |
| XXI | 3 | F1 | F1 | F1 | F3G2 | 0 | F1 | 0 | 0 |
|  | 1 | 0 | 0 | 0 | F2G1 | 0 | 0 | 0 | 0 |
| XXII | 3 | F1 | F1 | F1 | F3G2 | 0 | F1 | 0 | 0 |
|  | 1 | 0 | 0 | 0 | F2G1 | 0 | 0 | 0 | 0 |
| XXIII | 3 | 0 | G1 | 0 | F2G2 | 0 | F1 | 0 | 0 |
|  | 1 | 0 | 0 | 0 | F2G2 | 0 | 0 | 0 | 0 |
| XXIV | 3 | 0 | 0 | 0 | F1G1 | 0 | 0 | 0 | 0 |
|  | 1 | 0 | 0 | 0 | F1G1 | 0 | 0 | 0 | 0 |
| XXV | 3 | 0 | 0 | 0 | F2 | 0 | 0 | 0 | 0 |
|  | 1 | 0 | 0 | 0 | F1 | 0 | 0 | 0 | 0 |
| Comments |  | Fruit set | Fruit set | Fruit set | Tillering Fruit set | Fruit set *Rates: 1½ & ½ lb/A. | Fruit set | *Rates: Fruit set | Fruit set 1½ and ¼ lb/A. |

The use of many of the growth regulator compounds may be demonstrated by treatment of soybeans (*Soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders and, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml of acetone, adding 2 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants were observed within approximately three weeks after spray treatment and the results are tabulated below. The extent of growth regulatory effect on the plants was estimated on a scale of 0 to 10 and is also recorded in the following table:

TABLE 4

| | | GROWTH REGULATING EFFECTS ON TWO SPECIES | | |
|---|---|---|---|---|
| | | Soja max | Lycopersicum esculentum | |
| Comp'd. No. | Rate oz/A | Pod Count Percent in Comparison to Untreated Plants | Severity of Growth Regulating Effect | Fruit Count Percent in Comparison to Untreated Plants | Severity of Growth Regulating Effect |
| 4328 | 16 | 77 | 0 | 96 | 0 |
| | 4 | 105 | 0 | 77 | 0 |
| | 1 | 96 | 0 | 106 | 0 |

The information presented in tabular form herein will enable a worker in the art to make a selection from among the growth regulator compounds of the invention and to make some judgment with regard to application rates, depending upon the effect which is desired. It may be seen, for example, that total kills of some species of vegetation frequently occurs at application rates as high as 5 to 10 lb. per acre, whereas beneficial effects may be observed on living plants at application rates of 1 lb. per acre or less.

The growth regulator compounds are usually applied in combination with inert carriers or diluents, as in aqueous sprays, granules and dust formulations, in accordance with established practice in the art. An aqueous spray is usually prepared by mixing a wettable powder or emulsifiable concentrate formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the growth regulator formulations desirably contain from 0.1 percent to 95 percent by weight of a compound of formula (I) and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a nonphytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound spray is sprayed on the granules while they are being agitated in a suitable mixing apparatus, after which the granules are dried with a current of air during continued agitation.

I claim:

1. Compounds which have the general structural formula:

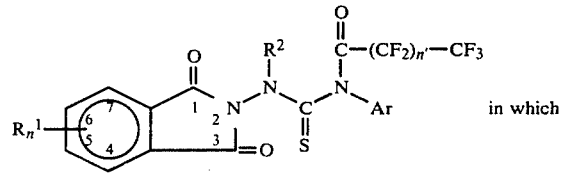

in which

R[1] is; $C_1$ to $C_4$ alkyl, nitro or halo and n is zero or an integer from 1 to 4

R[2] is $C_1$ to $C_4$ alkyl, or benzyl, n' is zero, 1 or 2 and

Ar is; naphthyl, phenyl or phenyl bearing thereon from one to three of the substituents: cyano, benzyloxy, nitro, bromo, chloro, trifluoromethyl and $C_1$ to $C_4$ alkyl, alkenyl, alkoxy, alkylthio and alkyl-substituted amino.

2. The compound according to claim 1 in which n is zero, R[2] is methyl, n' is zero and Ar is phenyl.

3. The compound according to claim 1 in which n is zero, R[2] is methyl, n' is 2 and Ar is phenyl.

4. The compound according to claim 1 in which n is zero, R[2] is methyl, n' is 1 and Ar is phenyl.

5. The compound according to claim 1 in which n is zero, R[2] is methyl, n' is zero and Ar is 2,4-dimethylphenyl.

6. The compound according to claim 1 in which n is zero, R[2] is methyl, n' is 1 and Ar is 2,4-dimethylphenyl.

7. The compound according to claim 1 in which n is zero, R[2] is methyl, n' is zero and Ar is 4-chlorophenyl.

8. The compound according to claim 1 in which n is zero, R[2] is methyl, n' is zero and Ar is 4-fluorophenyl.

9. The compound according to claim 1 in which n is zero, R[2] is methyl, n' is zero and Ar is 4-phenoxybenzyl.

10. The compound according to claim 1 in which n is zero, $R^2$ is methyl, n' is zero and Ar is 4-isopropylphenyl.

11. The compound according to claim 1 in which n is zero, $R^2$ is methyl, n' is zero and Ar is 4-ethoxyphenyl.

12. The compound according to claim 1 in which n is zero, $R^2$ is hydrogen, n' is zero and Ar is 4-isopropylphenyl.

13. The compound according to claim 1 in which n is zero, $R^2$ is methyl, n' is zero and Ar is 2,3-dimethylphenyl.

14. The compound according to claim 1 in which n is zero, $R^2$ is methyl, n' is zero and Ar is 4-bromophenyl.

15. The compound according to claim 1 in which n is zero, $R^2$ is methyl, n' is zero and Ar is 3,5-dimethylphenyl.

16. The compound according to claim 1 in which n is zero, $R^2$ is methyl, n' is zero and Ar is 4-carbethoxyphenyl.

17. The compound according to claim 1 in which n is zero, $R^2$ is ethyl, n' is zero and Ar is phenyl.

18. The compound according to claim 1 in which n is zero, $R^2$ is methyl, n' is zero and Ar is 3-fluorophenyl.

19. The compound according to claim 1 in which $R_n^1$ is 5-methyl, $R^2$ is methyl, n' is zero and Ar is phenyl.

20. The compound according to claim 1 in which n is zero, $R^2$ is methyl, n' is zero and Ar is 4-fluoro-2-methylphenyl.

21. The compound according to claim 1 in which n is zero, $R^2$ is allyl, n' is zero and Ar is phenyl.

22. The compound according to claim 1 in which n is zero, $R^2$ is methyl, n' is zero and Ar is 3-methylthiophenyl.

23. The compound according to claim 1 in which n is zero, $R^2$ is methyl, n' is zero and Ar is 4-phenoxyphenyl.

24. The compound according to claim 1 in which n is zero, $R^2$ is methyl, n' is zero and Ar is 1-naphthyl.

* * * * *